(12) United States Patent
Chinchoy et al.

(10) Patent No.: US 7,787,942 B2
(45) Date of Patent: *Aug. 31, 2010

(54) MECHANICAL VENTRICULAR PACING NON-CAPTURE DETECTION FOR A REFRACTORY PERIOD STIMULATION (RPS) PACING THERAPY USING AT LEAST ONE LEAD-BASED ACCELEROMETER

(75) Inventors: Edward Chinchoy, Golden Valley, MN (US); Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 460 days.

This patent is subject to a terminal disclaimer.

(21) Appl. No.: 11/742,210

(22) Filed: Apr. 30, 2007

(65) Prior Publication Data

US 2008/0269825 A1    Oct. 30, 2008

(51) Int. Cl.
*A61B 5/04* (2006.01)
(52) U.S. Cl. .................................................. 600/509
(58) Field of Classification Search ............... 607/4, 607/9, 17, 25, 28, 62; 600/509
See application file for complete search history.

(56) References Cited

U.S. PATENT DOCUMENTS

| 5,261,418 | A | 11/1993 | Ferek-Petric |
| 5,454,838 | A | 10/1995 | Vallana et al. |
| 5,628,777 | A | 5/1997 | Moberg et al. |
| 5,693,075 | A | 12/1997 | Plicchi et al. |
| 5,987,352 | A | 11/1999 | Klein et al. |
| 6,070,101 | A | 5/2000 | Struble et al. |
| 6,077,236 | A | 6/2000 | Cunningham |
| 6,473,645 | B1 | 10/2002 | Levine |
| 7,142,916 | B2 | 11/2006 | Deno et al. |
| 7,142,929 | B2 | 11/2006 | Gallagher |
| 7,277,761 | B2 * | 10/2007 | Shelchuk ............... 607/62 |
| 2004/0172079 | A1 * | 9/2004 | Chinchoy ............... 607/17 |
| 2005/0075676 | A1 * | 4/2005 | Deno et al. ............ 607/9 |
| 2005/0101998 | A1 * | 5/2005 | Kleckner et al. ....... 607/4 |
| 2006/0161211 | A1 | 7/2006 | Thompson et al. |

FOREIGN PATENT DOCUMENTS

| EP | 1222942 A | 7/2002 |
| WO | WO 03/020364 A | 3/2003 |
| WO | WO 03/037177 A | 5/2003 |

OTHER PUBLICATIONS

International Search Report, PCT/US2008/061747, Aug. 26, 2008, 6 pages.

* cited by examiner

*Primary Examiner*—George Manuel
*Assistant Examiner*—Robert N Wieland
(74) *Attorney, Agent, or Firm*—Stephen W. Bauer

(57) ABSTRACT

A system and method for monitoring at least one chamber of a heart (e.g., a left ventricular chamber) during delivery of a refractory period stimulation (RPS) therapy to determine if the desired non-capture (i.e., lack of ventricular mechanical capture due to refractory period stimulation) occurs. The system includes an implantable or external cardiac stimulation device in association with a set of leads such as epicardial, endocardial, and/or coronary sinus leads equipped with motion sensor(s). The device receives and processes acceleration sensor signals to determine a signal characteristic indicative of chamber capture due to pacing stimulus delivery, non-capture due to RPS therapy delivery, and/or contractile status based on the qualities of evoked response to pacing stimulation.

19 Claims, 8 Drawing Sheets

MECHANICAL VENTRICULAR PACING NON-CAPTURE DETECTION FOR A REFRACTORY PERIOD STIMULATION (RPS) PACING THERAPY USING AT LEAST ONE LEAD-BASED ACCELEROMETER

STATEMENT OF INCORPORATION BY REFERENCE

The present disclosure incorporates U.S. Pat. No. 7,142,929 entitled, "RECONFIGURABLE, FAULT TOLERANT MULTIPLE-ELECTRODE CARDIAC LEAD SYSTEMS" and U.S. Pat. No. 7,142,916 entitled, "CARDIAC PACING MODALITY HAVING IMPROVED BLANKING, TIMING, AND THERAPY DELIVERY METHODS FOR EXTRASYSTOLIC STIMULATION PACING THERAPY" as if fully set forth herein.

FIELD OF THE INVENTION

The present invention relates generally to implantable medical devices for monitoring or treating cardiac dysfunction by altering mechanical contractile function, and more particularly to devices and methods that require optimization of more than one electrical pulse for evoking the desired mechanical response during ventricular pacing, whether such pacing involves ventricles (i.e., bi-ventricular) or a single chamber delivery or combinations thereof (e.g., pacing pulses between ventricular configurations for contractility modulation, refractory period stimulation, stroke volume augmentation and the like).

BACKGROUND OF THE INVENTION

Determination of ventricular pacing capture thresholds is important in order to ensure that a patient is receiving a desired pacing therapy or for configuring the resulting mechanical ventricular contraction to one or more sequentially delivered pacing of various amplitudes and sequences. During the delivery of sub-threshold capture pulses or refractory period pulses to augment mechanical contraction, it is important to establish that such sub-threshold or refractory pulses do not by themselves result in a separate mechanical ventricular contraction, but results instead in the mechanical augmentation of the contraction initiated by the capturing pacing pulse. At least one based accelerometer is used to determine the relevant pacing parameters including the upper threshold, shortest interval(s), waveform, or timing relative to another cardiac event, in order that the clinician is able to set a range of electrical pulses that does not cause separate mechanical ventricular contractions with each electrical stimulus. Additionally, a range of parameters can be determined in order to optimally augment each ventricular contraction using the minimal amount of energy. The configuration of the electrical pulses may therefore be within a specified range as required to minimize the device energy required while ensuring that the desired therapy is maintained. In either case an algorithm can be incorporated in the device and/or programmer to use a motion sensor to measure the mechanical effects of one or more ventricular pacing pulses from either the left or right ventricular chamber in order to optimize the net mechanical ventricular effect by determining the range of parameters for electrical stimulation that results in a within a range of non-capturing electrical pacing pulse(s).

During normal cardiac function, the atria and ventricles observe consistent time-dependent relationships during the systolic (contractile) phase and the diastolic (relaxation) phase of the cardiac cycle. During cardiac dysfunction associated with pathological conditions or following cardiac-related surgical procedures, these time-dependent mechanical relationships are often altered. This alteration, when combined with the effects of weakened cardiac muscles, reduces the ability of the ventricle to generate contractile strength resulting in hemodynamic insufficiency.

Ventricular dyssynchrony following coronary artery bypass graft (CABG) surgery is a problem encountered relatively often, requiring post-operative temporary pacing. Atrio-biventricular pacing has been found to improve post-operative hemodynamics following such procedures.

Cardiac pacing may be applied to one or both ventricles or multiple heart chambers, including one or both atria, to improve cardiac chamber coordination, which in turn is thought to improve cardiac output and pumping efficiency. Clinical follow-up of patients pacing therapy has shown improvements in hemodynamic measures of cardiac function, ventricular volumes, and wall motion.

Implantable sensors for monitoring heart wall motion have been described or implemented for use in relation to the right ventricle. A sensor implanted in the heart mass for monitoring heart function by monitoring the momentum or velocity of the heart mass is generally disclosed in U.S. Pat. No. 5,454,838 issued to Vallana et al. A catheter for insertion into the ventricle for monitoring cardiac contractility having an acceleration transducer at or proximate the catheter tip is generally disclosed in U.S. Pat. No. 6,077,236 issued to Cunningham. Implantable leads incorporating accelerometer-based cardiac wall motion sensors are generally disclosed in U.S. Pat. No. 5,628,777 issued to Moberg, et al. A device for sensing natural heart acceleration is generally disclosed in U.S. Pat. No. 5,693,075, issued to Plicchi, et al. A system for myocardial tensiometery including a tensiometric element disposed at a location subject to bending due to cardiac contractions is generally disclosed in U.S. Pat. No. 5,261,418 issued to Ferek-Petric et al. All of the above-cited patents are hereby incorporated herein by reference in their entirety.

It is apparent from the above discussion that a need remains for providing a device and method for monitoring the mechanical effects of delivering one or more electrical pulses to the heart to ensure that a patient is in fact receiving a desired therapy.

SUMMARY OF THE INVENTION

The present invention provides a method and apparatus for monitoring mechanical pacing capture, by determining the bounds of pacing pulse parameters including amplitude, waveform, width, polarity, inter and intraventricular sequence and the like, for determining that the pulse that results in an augmentation of mechanical contraction of an original capturing electrical pulse, and does not instead initiate one or more separate ventricular contractions. In one embodiment, the present invention is realized in a pacing delivery system that includes an implantable multi-chamber pulse generator and associated lead system wherein a LV coronary sinus lead or left ventricular epicardial lead is provided with a sensor for detecting acceleration of the LV free wall or portions thereof, also referred to herein as "lateral wall" of the LV. In an alternative embodiment, a temporary, external pulse generator is coupled to temporary pacing leads including a temporary LV pacing lead is equipped with a motion sensor (e.g., an accelerometer).

In one form, a therapy known as refractory period stimulation (RPS) therapy one (or more) pacing pulses are delivered within (i.e., during) the refractory period of a cardiac chamber. Thus these pulses are not intended to mechanically capture the chamber and thus not result in an evoked response but enhance mechanical contractility on subsequent cardiac cycles. That is, the non-capturing RPS therapy provides augmented volume and flow from the chamber on successive cardiac cycles, versus causing separate ventricular contractions due to stimulation pulse delivery. RPS therapy delivery thus provides benefits for heart failure patients having diminished cardiac performance (i.e., cardiac insufficiency) and it has also been shown to improve cardiac perfusion following cardiac resuscitation therapy delivery (e.g., defibrillation).

According to the invention, during a temporal window following a mechanically- and/or electrically-sensed cardiac event (e.g., ventricular contraction) and while the RPS therapy delivery is occurring signals from the motion sensor are monitored to determine if the intended lack of mechanical capture event is detected for a given cardiac cycle. If not, the RPS therapy delivery parameters can be adjusted, a mode switch can occur to a different pacing mode, or the RPS therapy delivery can be terminated.

While the examples and depictions of the instant invention primarily involve placement of motion sensor(s) in, about, and around the LV, the invention should not be considered as so limited. In fact, the motion sensors can operate globally (e.g., disposed intermediate the atria and ventricles) or locally (e.g., disposed in, on, or about the right ventricle or one of the atrial chambers).

In one embodiment, the sensor comprises an accelerometer, which may be a uniaxial, biaxial, or triaxial accelerometer. Other types of sensors capable of generating a signal proportional to LV lateral wall acceleration can be utilized (e.g., tensiometric, pressure sensors and the like). The sensor can be disposed in or proximate the mid- or mid-basal LV free wall segments.

The implantable or external system receives and processes the acceleration sensor signal to determine whether mechanical pacing capture is actually occurring. Signal processing is performed to monitor and/or measure any acceleration signal (s) during a period of time following delivery of the RPS therapy. Various metrics related to capture can be stored with other parametric or physiologic data for monitoring and/or diagnostic purposes via telemetry to local or remote clinicians.

DETAILED DESCRIPTION OF THE INVENTION

As indicated above, the present invention is directed toward providing a method and apparatus for monitoring one of more chambers of a heart for optimizing electrical pulses using mechanical parameters based on monitoring ventricular wall acceleration (e.g., LV free wall). In particular, the present invention is useful for ensuring non-capture of one or more chambers of a heart during RPS therapy delivery to treat heart failure. The present invention is also useful in ensuring non-capture during temporary pacing applied for treating post-operative ventricular dyssynchrony. As such, the present invention may be embodied in an implantable cardiac pacing system including a dual chamber or multichamber pacemaker and associated set of leads. Alternatively, the present invention may be embodied in a temporary pacing system including an external pacing device with associated temporary pacing leads.

Figure 1A:
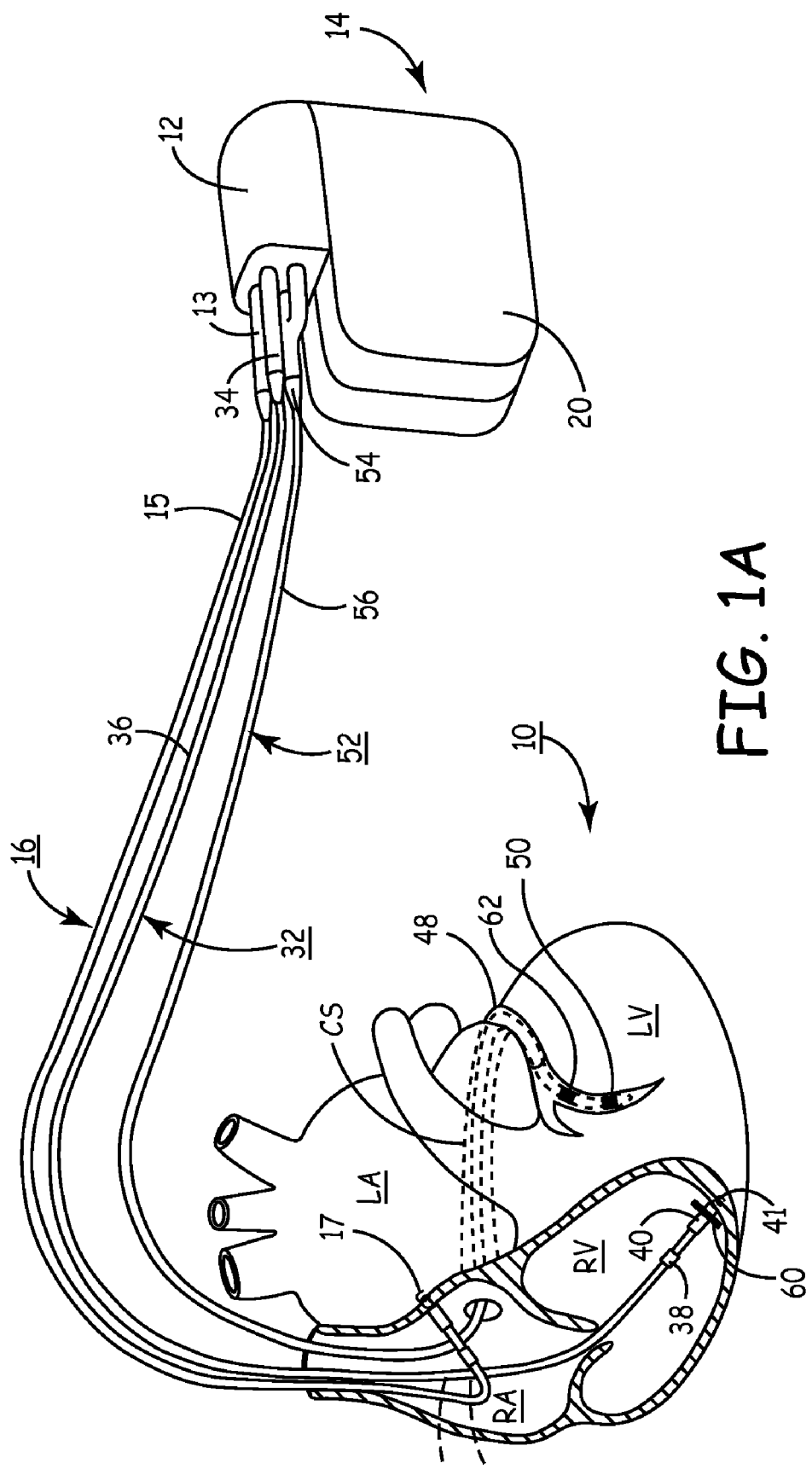
FIG. 1A depicts an exemplary implantable, multi-chamber cardiac pacemaker in which the present invention may be implemented.

FIG. 1A depicts an exemplary implantable, multi-chamber cardiac pacemaker 14 in which the present invention may be implemented. The multi-chamber pacemaker 14 is provided for restoring ventricular synchrony by delivering pacing pulses to one or more heart chambers as needed to control the heart activation sequence. The pacemaker 14 is shown in communication with a patient's heart 10 by way of three leads 16,32,52. The heart 10 is shown in a partially cut-away view illustrating the upper heart chambers, the right atrium (RA) and left atrium (LA), and the lower heart chambers, the right ventricle (RV) and LV, and the coronary sinus (CS) extending from the opening in the RA laterally around the atria to form the great cardiac vein 48, which branches to form inferior cardiac veins.

The pacemaker 14, also referred to herein as the "implantable pulse generator" or "IPG," is implanted subcutaneously in a patient's body between the skin and the ribs. Three transvenous endocardial leads 16,32,52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38,40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals. RV lead 32 may optionally include a RV wall motion sensor 60. RV wall motion sensor 60 may be positioned into or proximate the RV apex for detecting motion or acceleration of the RV apical region. Implantation of an acceleration sensor in the right ventricle is generally disclosed in the above-cited U.S. Pat. No. 5,693,075 issued to Plicchi, et al.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a cardiac vein branching from the great cardiac vein 48.

In accordance with the present invention, the coronary sinus lead 52 is provided with a sensor 62 capable of generating a signal proportional to the acceleration of the left ventricular free wall. Sensor 62 is preferably embodied as a uniaxial, biaxial, or triaxial accelerometer contained in a capsule of a relatively small size and diameter such that it may be included in a coronary sinus lead without substantially increasing the lead diameter or impairing the ability to steer the lead to a left ventricular pacing and sensing site. Radial acceleration may not be as valuable in assessing LV wall acceleration and optimizing pacing intervals as longitudinal acceleration, therefore, a uniaxial accelerometer may be adequate for these purposes. Sensor 62 may alternatively be provided as another type of sensor such as an optical, acoustical sensor or a sensor having piezoelectric, inductive, capacitive, resistive, or other elements which produce a variable signal proportional to left ventricular acceleration or from which variations in LV acceleration can be derived. Sensor 62 is preferably located on CS lead 52 such that when CS lead 52 is positioned for LV pacing and sensing, sensor 62 is located approximately over the LV free wall mid-lateral to mid-basal segments. The depicted positions of the leads and electrodes shown in FIG. 1A in or about the right and left heart chambers are approximate and merely exemplary. For example, an LV acceleration sensor 62 may alternatively be located on CS lead 52 such that sensor 62 is positioned in the coronary sinus, in the great cardiac vein, or in any accessible inferior cardiac vein. Furthermore, it is recognized that alternative leads and pace/sense electrodes that are adapted for placement at pacing or sensing sites on or in or relative to the RA, LA, RV and LV may be used in conjunction with the present invention.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

Figure 1B:
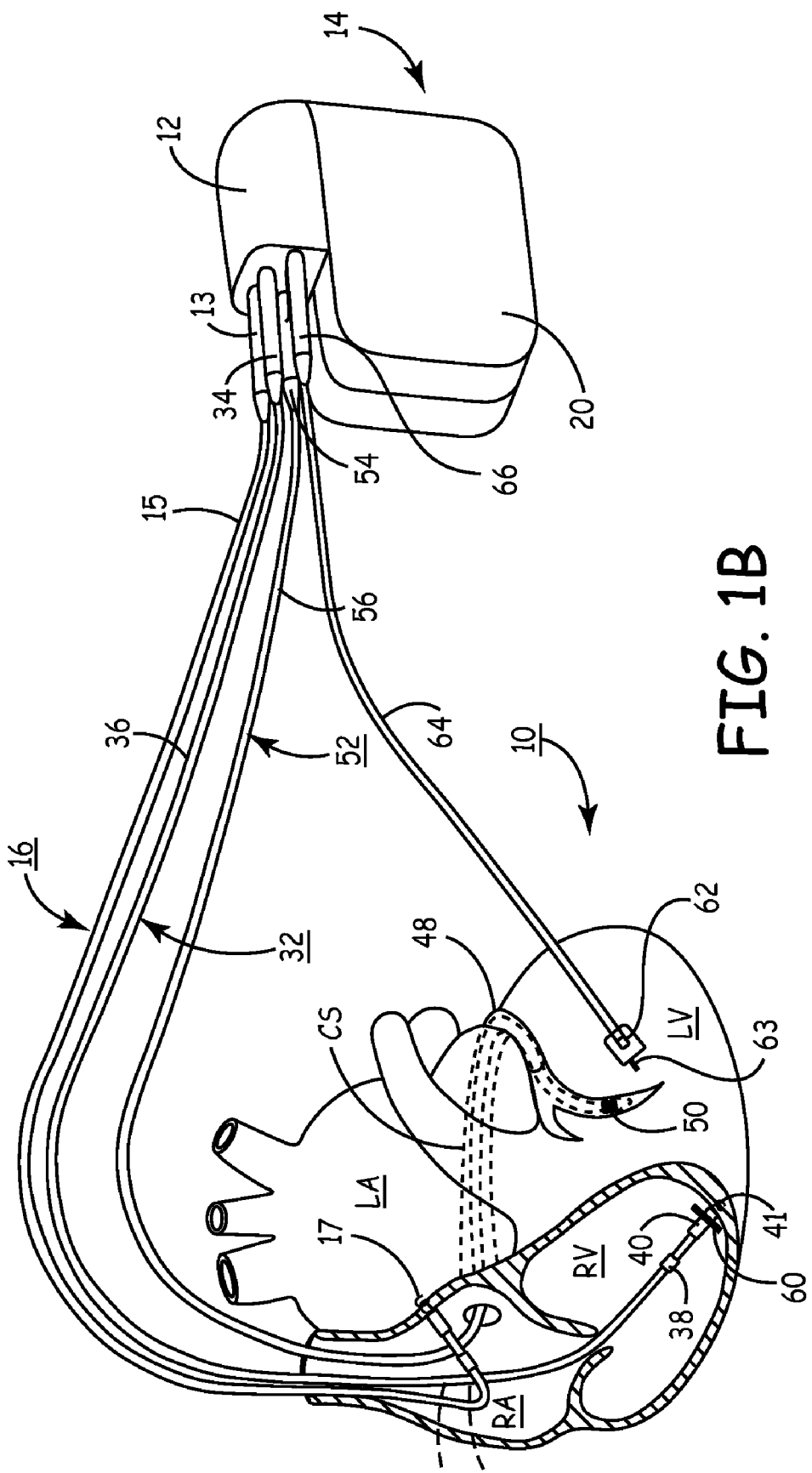
FIG. 1B depicts an exemplary implantable, multi-chamber cardiac pacemaker coupled to a patient's heart via transvenous endocardial leads and an additional left ventricular epicardial lead equipped with acceleration sensor.

FIG. 1B depicts an exemplary implantable, multi-chamber cardiac pacemaker coupled to a patient's heart via transvenous endocardial leads and an additional left ventricular epicardial lead equipped with acceleration sensor 62. Patients may already be implanted with a transvenous lead system that includes a coronary sinus lead 52 that is not equipped with an acceleration sensor. Such patients may benefit from the placement of an epicardial lead 64 equipped with an acceleration sensor 62 coupled to IPG 14 via a connector 66 so as to provide an LV acceleration signal for use in a closed-loop feedback system for providing PESP therapy at optimal pacing intervals.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for pacing, EGM sensing and acceleration monitoring, eliminating the need for a coronary sinus lead. Alternatively, it may be desirable to deploy a small diameter coronary sinus lead for LV pacing and EGM sensing with a separate LV epicardial lead positioned for sensing LV lateral wall acceleration.

The embodiment generally shown in FIG. 1B is particularly advantageous for use in selecting one or more RPS therapy delivery pacing sites. With epicardial lead 64 fixed at a desired location for assessing LV lateral wall acceleration, the effect of pacing at different locations in one or more heart chambers can be evaluated by deploying the transvenous pacing leads 16,32 and 52 to different locations (e.g., to tissue locations that remain refractory longer than other locations, such as infracted tissue). In particular, coronary sinus lead 52 may be advanced to different locations until one or more such locations are identified based on analysis of the signal from LV acceleration sensor 62. By providing acceleration sensor 62 on a separate, epicardial lead 64, the position of RPS therapy delivery electrode 50, provided on coronary sinus lead 52, may be adjusted independently of sensor 62. If the position of pacing electrode 50 needs adjusting, acceleration sensor 62 may remain fixed at a desired measurement site on the LV lateral wall thereby allowing comparisons to be made between measurements repeated at the same location for different pacing intervals and/or pacing sites. That is, relatively longer or additional RPS pulses can be delivered without capturing the chamber and presumably increased benefits of chronic RPS therapy delivery can be realized.

Figure 2:
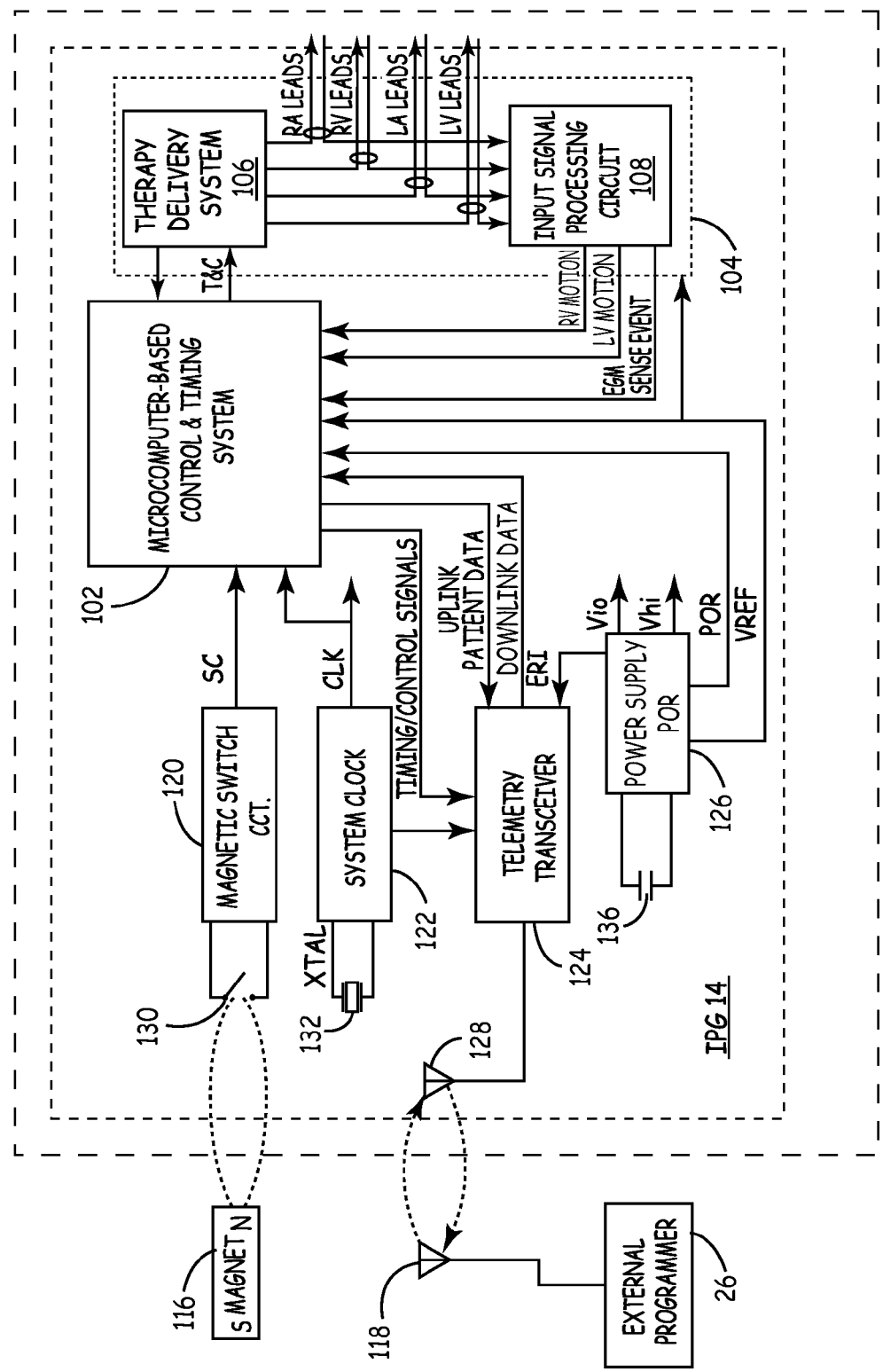
FIG. 2 is a schematic block diagram of an exemplary multi-chamber implantable pulse generator that provides delivery of a RPS therapy and is capable of processing left ventricular acceleration signal input.

FIG. 2 is a schematic block diagram of an exemplary multi-chamber IPG 14, such as that shown in FIG. 1A or 1B, that provides delivery of a PESP therapy and is capable of processing left ventricular acceleration signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A-A), atrial-ventricular (A-V), and ventricular-ventricular (V-V) intervals.

Physiologic input signal processing circuit 108 is provided for receiving cardiac electrogram (EGM) signals for determining a patient's heart rhythm. Physiologic input signal processing circuit 108 additionally receives signals from LV wall acceleration sensor 62, and optionally RV wall motion sensor 60, and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable pacing intervals is preferably based on a determination of left ventricular lateral wall acceleration derived from sensor 62 signals as will be described in greater detail below.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber pacemaker circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including acceleration data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or LV acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect. The intervals at which pacing pulses are delivered are preferably determined based on an assessment of LV wall acceleration data.

As such, input signal processing circuit 108 further includes signal processing circuitry for receiving, amplifying, filtering, averaging, digitizing or otherwise processing the LV wall acceleration sensor signal. If additional acceleration or other wall motion sensors are included in the associated lead system, for example a RV wall motion sensor, additional wall motion signal processing circuitry may be provided as needed. Acceleration signal processing circuitry is further provided for detection and/or determination of one or more acceleration signal characteristics such as maximum and minimum peak amplitudes, slopes, integrals, or other time or frequency domain signal characteristics that may be used as indices of acceleration. Acceleration data from an LV lateral wall acceleration sensor signal are made available to control and timing system 102 via LV MOTION signal line for use in algorithms performed for identifying pacing intervals producing optimal LV acceleration. If an RV wall motion sensor is present, an additional RV MOTION signal line provides RV wall motion signal data to control and timing system 102.

Figure 3:
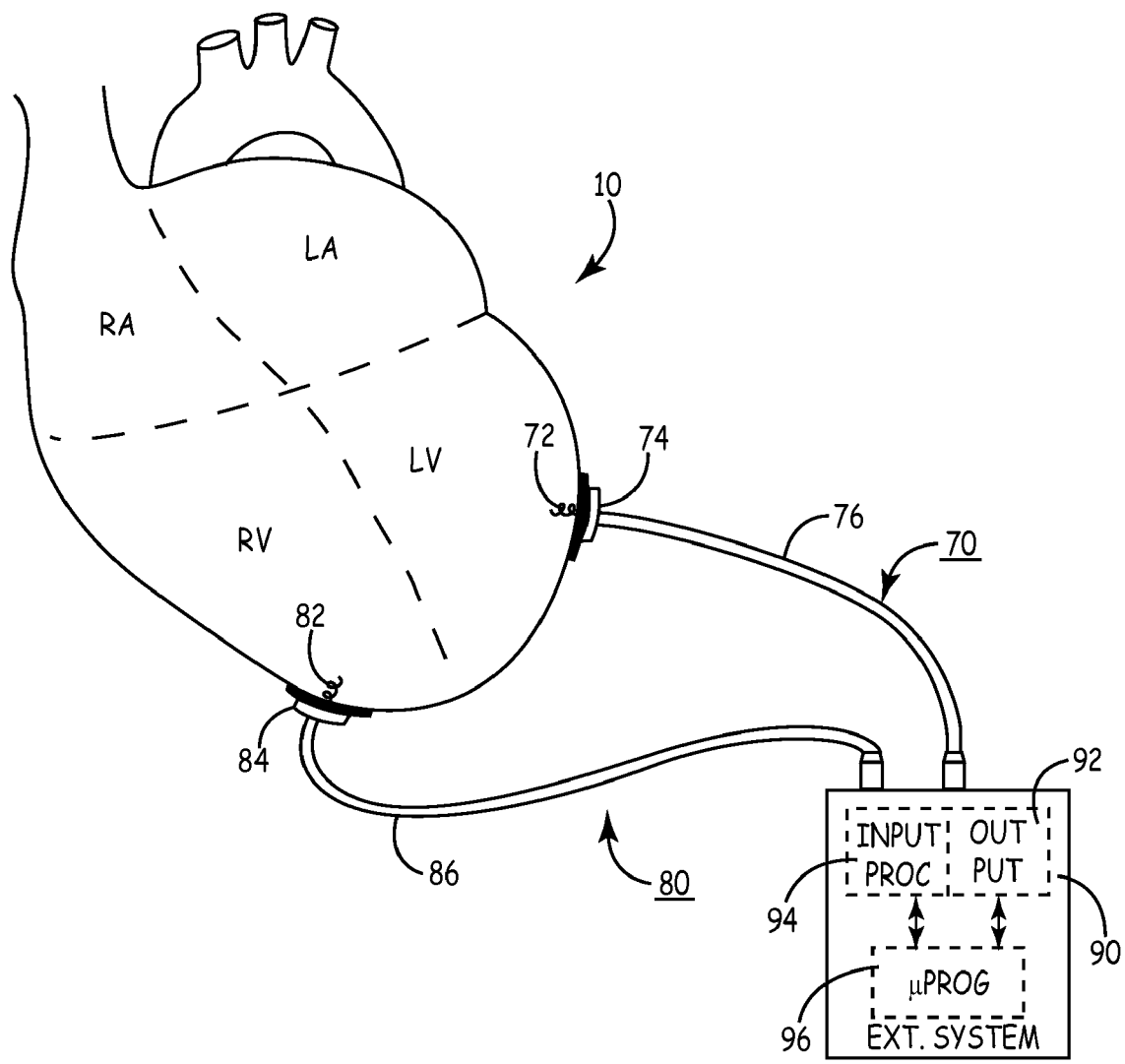
FIG. 3 depicts an alternative, epicardial lead system coupled to a patient's heart.

FIG. 3 depicts an alternative, epicardial lead system coupled to a patient's heart. Epicardial leads may be used in conjunction with either chronically implantable or temporary external pacing systems. In the embodiment shown, RV epicardial lead 80 is shown fixed via an active fixation electrode 82 near the apex of the RV such that the active fixation electrode 82 is positioned in contact with the RV epicardial tissue for pacing and sensing in the right ventricle. RV epicardial lead 80 may optionally be equipped with an RV wall motion sensor 84 for detecting motion or acceleration of the RV apical region. LV epicardial lead 70 is shown fixed via an active fixation electrode 72 in the LV free wall such that active fixation electrode 72 is positioned in contact with the LV epicardial tissue for pacing and sensing in the left ventricle. LV epicardial lead 70 is equipped with an acceleration sensor 74 for detecting acceleration of the LV free wall. Epicardial lead systems may further include epicardial RA and/or LA leads. Various combinations of epicardial and transvenous endocardial leads are also possible for use with biventricular or multichamber cardiac stimulation systems.

In FIG. 3, RV and LV epicardial leads 70 and 80 are shown coupled to an external, temporary cardiac pacing device 90. External pacing device 90 is preferably a microprocessor controlled device including microprocessor 96 with associated RAM and ROM for storing and executing firmware and programmable software for controlling the delivery of pacing pulses to LV and RV pace/sense electrodes 72 and 82. External device 90 receives signals from and delivers electrical pulses to LV and RV pace/sense electrodes 72 and 82 via conductors included in LV epicardial lead body 76 and RV epicardial lead body 86. EGM signals, LV lateral wall acceleration signals, and optionally RV wall motion signals are received as input to input signal processing circuitry 94. Pacing impulses are delivered by output circuitry 92 as needed, based on sensed EGM signals, at intervals determined based on signals received from LV acceleration sensor 74 as will be described in greater detail below. It is recognized that an epicardial lead system such as that shown in FIG. 3 that includes an LV acceleration sensor and optionally an RV wall motion sensor may alternatively be used in conjunction with an implantable pacing system, such as the multi-chamber system described above and shown in FIGS. 1A and 2.

External device 90 of FIG. 3 and implantable device 14 of FIGS. 1A, 1B and 2 are shown to provide both sensing/monitoring and pacing delivery capabilities. Certain device features may be enabled or disabled as desired. For example, monitoring of LV lateral wall acceleration without delivery of a RPS therapy may be desired. Acceleration sensor signal data may therefore be received, processed and stored by an implantable or external device for later analysis and review by a clinician as well as for comparison to improve detection of (un-desired) capture due to RPS therapy delivery. For example, the wall motion from a capturing pulse can be used as a template or for morphological analysis in an attempt to determine whether one or more RPS therapy pulses captured a chamber. Also, analysis of such capturing stimuli can be used to monitor improvement in a patient's contractility (presumably as a result of RPS therapy delivery and other palliative therapies).

Figure 4:
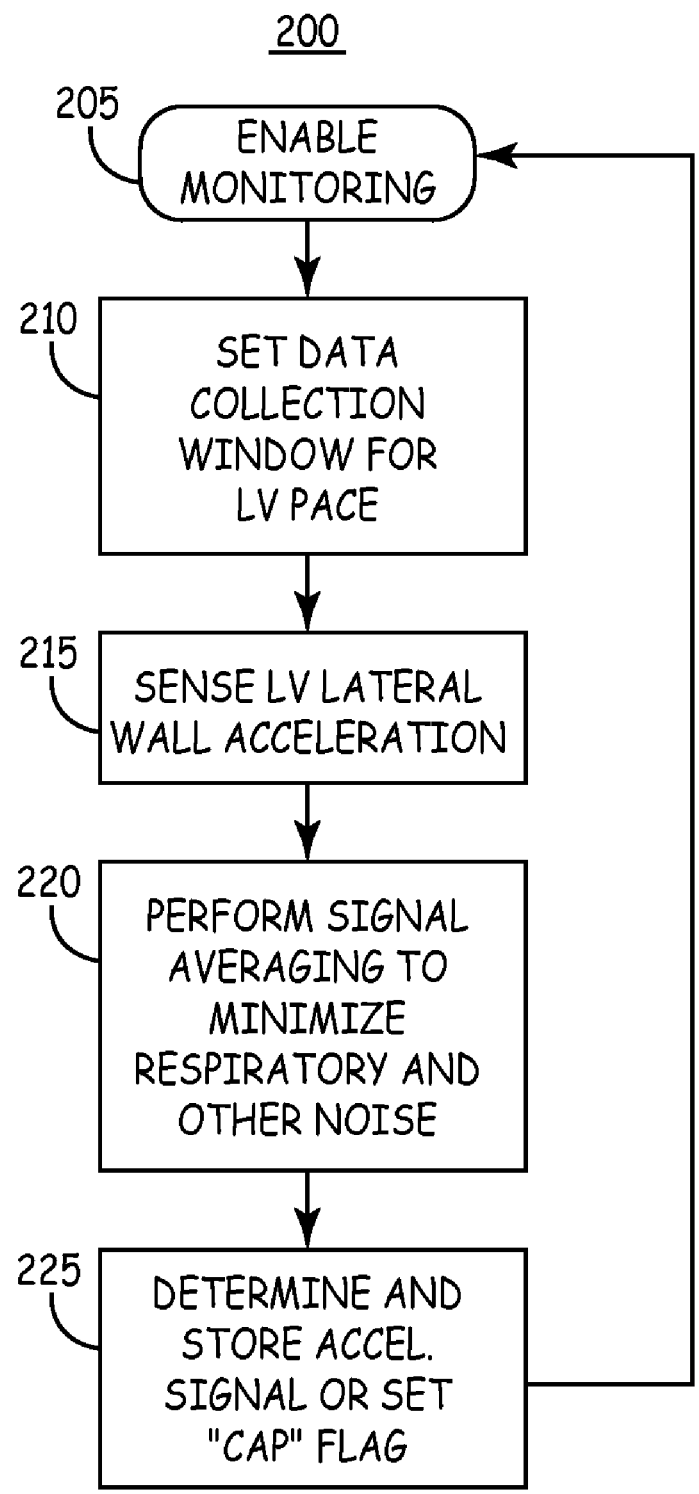
FIG. 4 is a flow chart providing an overview of a method for monitoring LV non-capture based on sensing LV lateral wall acceleration.

FIG. 4 is a flow chart providing an overview of a method for monitoring cardiac contractility based on sensing LV lateral wall acceleration. Monitoring may be performed on an acute or chronic basis, using an implanted or external device in association with a LV lead equipped with an acceleration sensor as described above. Monitoring may be performed for diagnostic, prognostic, or therapy evaluation purposes. Therefore, monitoring may be performed post-operatively, during drug infusion, subsequent to a medical or device-delivered therapy, or on a chronic basis for ambulatory monitoring of patient status or therapy optimization and evaluation, Evaluation of LV contractility is of interest for both diagnostic and therapeutic applications. Thus, it is recognized, that aspects of the present invention may be employed for cardiac monitoring purposes with or without optimization or evaluation of a therapy. As such, method 200 summarized in FIG. 4 may be implemented in an implantable or external device, such as the devices shown in FIGS. 1A, 1B and FIG. 3, for monitoring LV contractility by deriving and storing an index of cardiac contractility based on an LV wall acceleration signal. The therapy delivery functions of such devices may be selectively disabled or, if enabled, the RPS therapy optimization and contractility monitoring based on LV acceleration may be selectively enabled or disabled such that monitoring function only are enabled. Method 200 may alternatively be implemented in internal or external devices that do not include therapy delivery capabilities but, in association with an LV lead equipped with an acceleration sensor, are capable of processing and storing LV acceleration data.

Monitoring may be performed on a continuous, periodic or triggered basis. For example, LV function may be evaluated on a periodic basis such as hourly, daily, weekly, or otherwise. Additionally or alternatively, LV function may be evaluated on a triggered basis, which may be a manual or automatic trigger. Automatic triggers may be designed to occur upon the detection of predetermined conditions during which LV function evaluation is desired, such as a particular heart rate range, activity, or other conditions.

Manual triggers for LV acceleration sensing and/or data storage may be delivered by a clinician or by a patient, for example when the patient feels symptomatic. Methods for manually triggering the storage of physiological data in an implantable device are generally described in U.S. Pat. No. 5,987,352 issued to Klein, et al., hereby incorporated herein by reference in its entirety.

Method 200 begins at step 205 when monitoring is enabled according to a periodic, continuous or triggered mode of operation. At step 210, a data collection window is set. LV acceleration data is preferably collected during ventricular systole and most preferably during the isovolumic contraction phase. In one embodiment, the data collection window is a fixed time interval triggered by a sensed R-wave or a ventricular pacing pulse. The data collection window may begin immediately after, or following a predefined interval after delivery of a first or subsequent RPS therapy pulse (herein a primary "P1" pacing pulse and/or additional pulses denoted as "P2") and preferably extending for a period of time thereafter.

Figure 5:
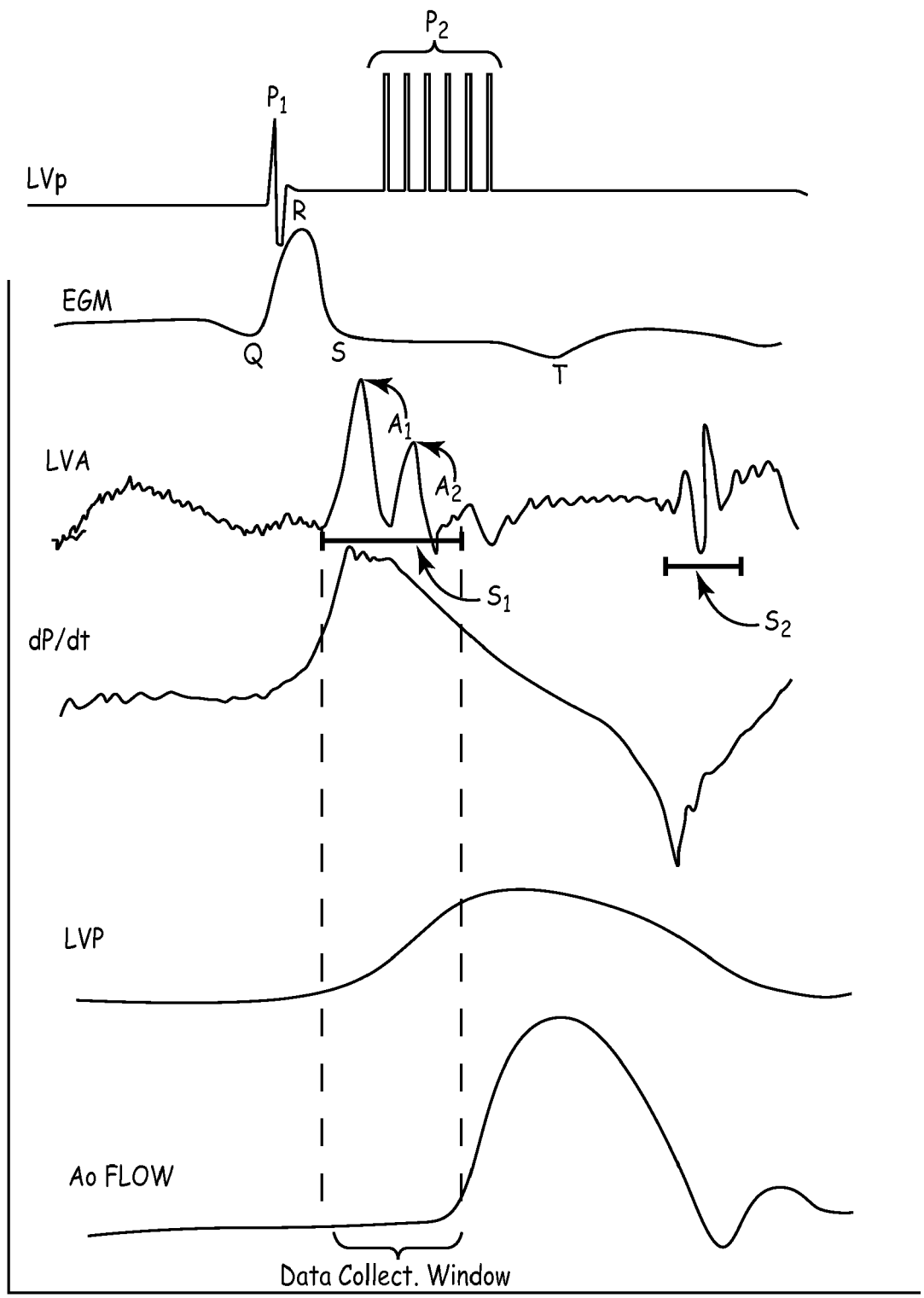
FIG. 5 is a plot of sample LV lateral wall acceleration data and simultaneous hemodynamic and electrical data acquired during one cardiac cycle wherein a first depolarization (P1) is followed by delivery of at least one second pacing stimulus (P2) delivered during the refractory period.

FIG. 5 is a plot 500 of sample LV lateral wall acceleration data (LVA) 502 and simultaneous hemodynamic and electrical data acquired during one cardiac cycle wherein a first evoked depolarization due to a first pacing stimulus (P1) is followed by additional RPS therapy stimulus (P2) delivered within the refractory period (represented by dashed line 504). That is, the trace 508 appearing below the pacing stimulus trace 506 represents a ventricular EGM signal showing a typical (evoked) QRS complex of relatively large amplitude followed by a relatively smaller amplitude T-wave. The QRS complex marks the electrical activation of the myocardial tissue, causing depolarization and subsequent contraction of the myocardial fibers. The LVA trace 502 represents a nominal acceleration signal obtained from a motion sensor (e.g., an accelerometer) placed to measure LV free wall acceleration. LVA is seen to reach a peak shortly after the QRS complex arrives. The S1 phase indicated on plot 500 corresponds to the isovolumic contraction phase of ventricular systole and is associated with the first heart sound (S1) which occurs at the beginning of systole. LV free wall acceleration during this isovolumic phase, also referred to herein as "S1 phase", is not constant. In the example shown, LVA forms at least two distinct two peaks, $A_1$ and $A_2$, during the S1 phase. Varying conditions may result in one, two, three or possibly more LVA peaks during the isovolumic contraction phase. During isovolumic contraction, a large increase in LV pressure (LVP) denoted by reference numeral 512 is generated as illustrated in plot 500. LVP rises rapidly during the isovolumic phase (as illustrated by trace 510) which depicts an exemplary temporal derivative of LVP (dP/dt). As LVP reaches a peak, the aortic valve opens, initiating the systolic ejection phase and an associated increase in aortic flow (Ao FLOW) as illustrated by trace 514. After LVP falls, the aortic valve closes. During this phase, associated with the second heart sound, S2, the LVA signal 502 exhibits one or more peaks that are typically lower in amplitude than the S1 peaks.

While not depicted in FIG. 5, assuming undesirable capture due to the P2 stimulus subsequent cardiac cycles will exhibit pronounced augmentation of pressure and flow typically characterized by two peak pressure signals. Thus, such subsequent cycles can also be monitored to determine if a prior RPS pulse or pulses captured the heart. However, the acceleration signal due capture are readily discernible as those depicted in FIG. 5 due to the P1 pacing stimulus (e.g., A1, A2, etc.) although they will appear as a second series of peak motion signals approximately when the S2 heart sound would have been detected but for the delivery of the extrasystolic stimulation.

Referring again to FIG. 4, method 200 senses the LV lateral wall acceleration signal at step 215 during the data collection window set at step 210 such that it extends approximately from the start to the end of the isovolumic contraction phase. Preferably the acceleration sensor is implanted in or proximate to the LV free wall as described above. More preferably, an LV acceleration signal is obtained from an accelerometer located on a coronary sinus lead or an epicardial lead positioned such that the accelerometer is situated over the mid-lateral, mid-basal or basal segment of the left ventricular free wall. At step 215, the LV lateral wall acceleration signal is acquired over a number of cardiac cycles.

At step 225, the acceleration signal is determined and stored or a logical flag is set (e.g., non-capture confirmed, non-capture suspect, loss of capture). Additional information may be stored with the LVA data such as other sensed physiologic data and/or a time and date label and/or other parametric information. When method 200 is executed by an external system, LVA data may be displayed in real-time or stored and presented following a monitoring episode. When method is executed by an implanted device, LVA data may be stored for later uplinking to an external device for display and review by a physician. Such data could include percent paced capture for the LV or the like.

Figure 6:
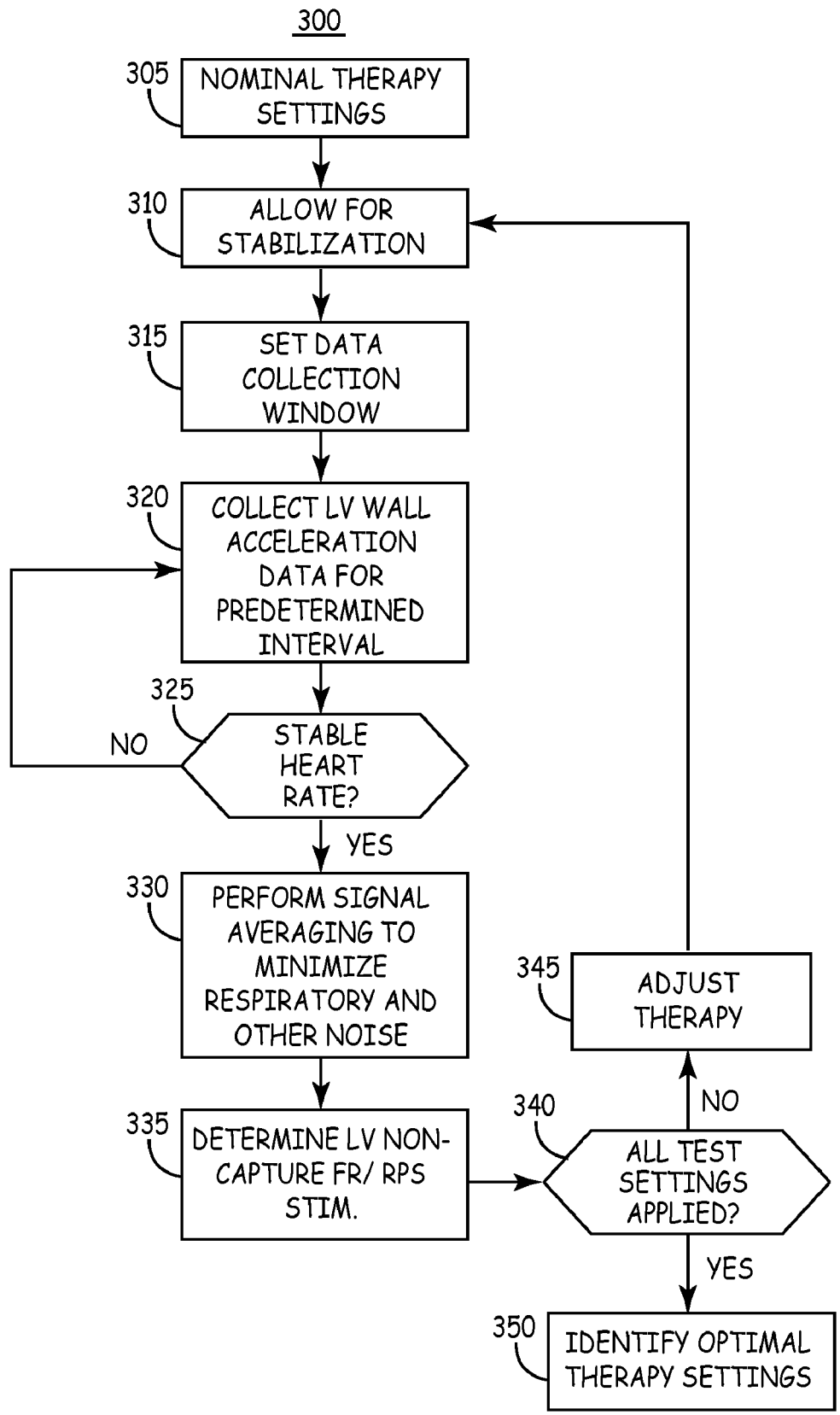
FIG. 6 is a flow chart summarizing steps included in a method for confirming that no evoked response occurs due to delivery of RPS therapy based on left ventricular lateral wall acceleration signal collected subsequent to stimulus—denoted as a P2 pulse herein.

As indicated previously, LV lateral wall acceleration may be monitored for both capture of a P1 pulse and confirmation of non-capture of the P2 pacing pulse(s). FIG. 6 is a flow chart summarizing steps included in a method for monitoring LV non-capture due to RPS delivery based on LV lateral wall acceleration. Method 300 begins at step 305 wherein a therapy is delivered or administered at nominal settings or dosages. A therapy may be a single or dual chamber (and/or multi-site electrode) form of RPS therapy, a therapy for treating myocardial ischemia, a medical therapy, or any other known therapy for improving cardiac contractility. As will be described, an iterative procedure may be performed for determining the optimal settings for RPS delivery (e.g., amplitude, number of pulses, polarity, pulse widths, intervals, etc.) or dosages at which a therapy should be delivered for ensuring LV non-capture based on a measurement of LV free wall acceleration.

Depending on the type of therapy administered, an optional stabilization period may be provided at step 310 to allow the hemodynamic response to a change in therapy to stabilize prior to monitoring LVA. A stabilization period may range from several seconds, to minutes, hours or even days depending on the therapy being delivered.

At step 315 a data collection window is set, preferably extending just beyond delivery of an LV pacing pulse. At step 320, the LVA signal is sampled during the data collection window for each cardiac cycle during a predetermined time interval and/or for a predetermined number of cardiac cycles. In an alternative embodiment, the LVA signal may be acquired continuously during the predetermined time interval or number of cardiac cycles and subsequently processed to separate components associated with the isovolumic contraction phase, and more particularly with the first acceleration peak during isovolumic contraction. The time interval or number of cardiac cycles preferably extends over at least one respiration cycle such that averaging of the LVA signal over a respiration cycle may be performed to eliminate variations in the LVA measurements due to respiration. In one embodiment, the start and stop of LVA data acquisition may be triggered by sensing a respiration cycle. Respiration may be detected based on impedance measurements or other methods known in the art.

At decision step 325, verification of a stable heart rate during the data acquisition interval is performed. Heart rate instability, such as the presence of ectopic heart beats or other irregularities, would produce anomalous LVA data. As such, the heart rate preferably stays within a specified range. In one embodiment, heart rate stability may be verified by determining the average and standard deviation of the cardiac cycle length during the data acquisition period. The cardiac cycle length is determined as the interval between consecutive ventricular events including ventricular pacing pulses and any sensed R-waves. If the average cardiac cycle length or its standard deviation falls outside a predefined range, the data is considered unreliable. Data acquisition may be repeated by returning to step 315 until reliable data is collected for the current therapy settings.

At step 330, signal averaging is performed to minimize the effects of respiration-related or other noise. The signals acquired during each cardiac cycle over the data collection interval are averaged to obtain an overall average LVA signal. At step 335, one or more signal features are determined from the averaged LVA signal as an indication of non-capture of a ventricle due to RPS therapy delivery (e.g., non-capture of a series of maximum acceleration signals following pacing delivery—P1 or P2) at the nominal or modified therapy settings and stored in device memory with corresponding physiologic information.

If all therapy settings need to be adjusted or a regime of nominal testing signals have yet to be applied, as determined at decision step 340, the method 300 adjusts the therapy at step 345 and returns to optional step 310 and repeats steps 315 through 335 to determine, based upon the LVA signals whether non-capture of the ventricle has occurred due to the P2 RPS stimulation. Once all test settings have been applied, the optimal setting is identified based on the stored LVA data at step 350.

Figure 7:
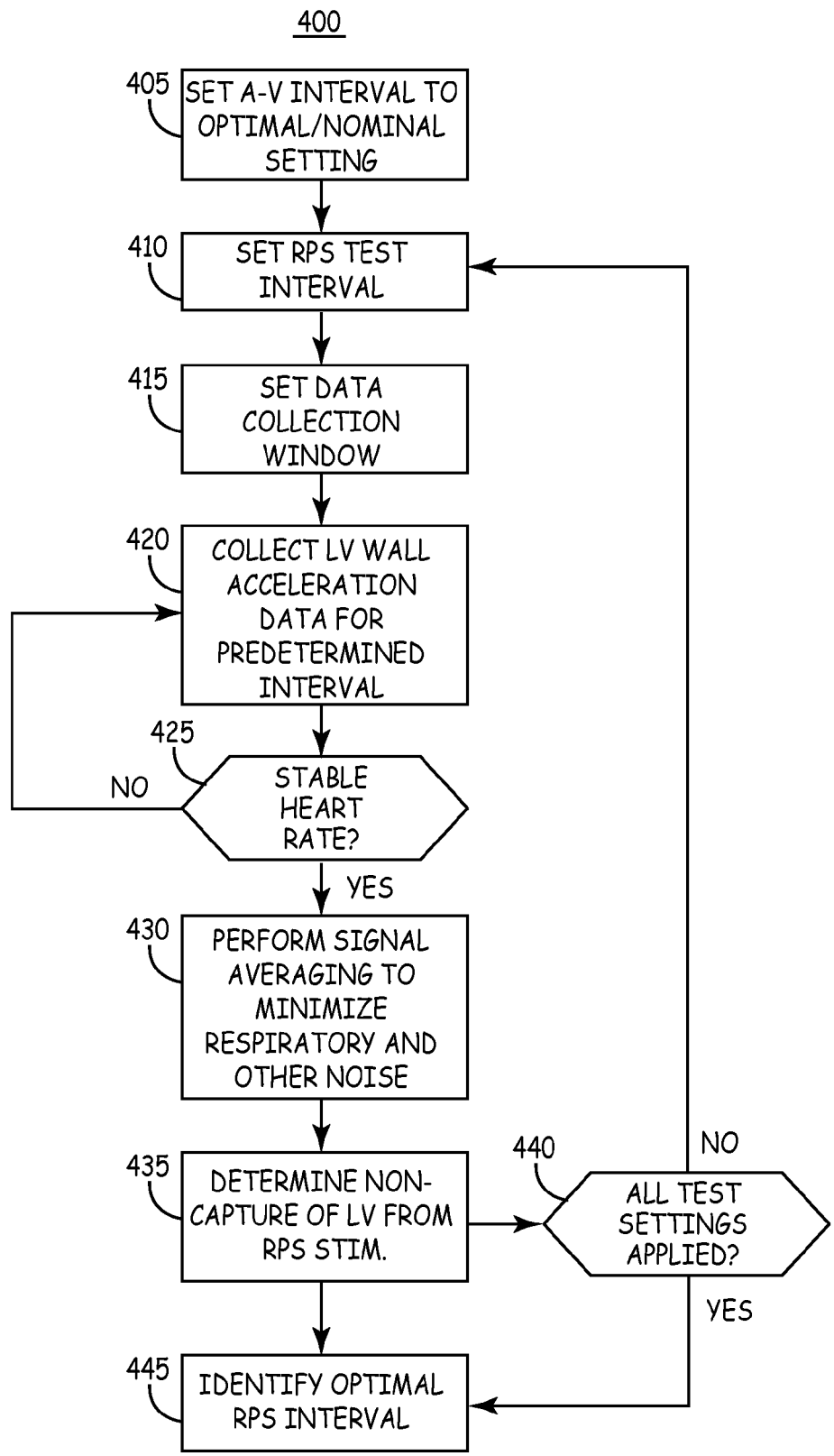
FIG. 7a flow chart summarizing steps included in a method for determining non-capture of the LV due to RPS therapy delivery based on left ventricular acceleration.

FIG. 7 is a flow chart summarizing steps included in a method for determining LV chamber non-capture based on LV acceleration. At step 405, the A-V interval is programmed to a previously determined optimal or nominal setting. An A-V interval optimization procedure may be performed prior to delivering PESP therapy. The A-V interval may be optimized based on methods known in the art. For example, an A-V interval may be selected as the shortest A-V interval that does not truncate ventricular filling based on echocardiographic evaluation. Alternatively, an optimal A-V interval may be selected based on RV apical motion as detected by an accelerometer placed at the RV apex. The A-V interval may alternatively be set to a nominal setting at step 405.

At step 410, as applicable a V-V interval is set to a test interval. A range of test intervals are predefined and may be delivered in a random, generally increasing, or generally decreasing fashion. A range of test intervals may include intervals that result in the right ventricle being paced prior to the left ventricle and intervals that result in the left ventricle being paced prior to the right ventricle and simultaneous right and left ventricular pacing. A set of exemplary test intervals includes right ventricular pacing 20 ms and 40 ms prior to LV pacing, simultaneous LV and RV pacing (a V-V interval of 0 ms), and LV pacing 20 ms and 40 ms prior to the RV.

Method 400 proceeds to determine whether ventricular capture is occurring due to the P2 pacing stimulation. A data collection window is set at step 415, and LVA data is collected for a predetermined time interval or number of cardiac cycles at step 420 during the data collection window applied to each cardiac cycle. After verifying a stable heart rate at step 425, signal averaging is performed at step 430 allowing an average peak amplitude or average peak-to-peak difference of the first acceleration peak ($A_1$) during the period of time when LV capture would be expected to occur and method 400 returns to step 410 to continue monitoring for LV non-capture in a temporal window subsequent to the P1 capturing pulse and for all or a portion of the refractory period of the chamber (e.g., periodically, continuously or aperiodically)

When method 400 is executed by an external pacing system, LVA data is available for real-time display or stored and presented following capture confirmation. An attending clinician may program the LV pacing thresholds or the external system may adjust the thresholds to confirm LV capture due to P1 stimulus and desirable LV non-capture due to RPS therapy delivery. When method 400 for identifying LV capture thresholds is executed by an implanted device, LVA data may be processed and stored for later uplinking to an external device for display and review by a physician. The implanted device can automatically adjust the pacing pulse parameters (e.g., amplitude, duration, polarity, etc.).

Thus a method and apparatus have been described for monitoring LV chamber capture and/or optimizing threshold to ensure LV non-capture (automatically or manually) and/or changes in contractility based on LV lateral wall acceleration measured using a LV lead equipped with an acceleration sensor. The methods described herein may advantageously be applied in numerous cardiac monitoring or therapy modalities including chronic or acute applications associated with implantable or external devices.

As is known in the art, besides the transducers described hereinabove, other types of transducers may be used provided, in general, that such transducers are hermetically sealed, are fabricated (on least on the exterior surfaces) of substantially biocompatible materials and appropriately dimensioned for a given application. With respect to appropriate dimension, a transducer intended to transvenous deployment should be susceptible of catheter or over-the-wire delivery. Thus, the radial dimension should be on the order of less than about 11 French and preferably about less than eight French. Also, the transducer should be somewhat supple, and not too long, in the longitudinal dimension so that the transducer can safely navigate the venous system, pass through the coronary sinus and enter vessels branching from the coronary sinus (e.g., the great cardiac vein, and the like). These dimensions can be relaxed for a transducer intended for deployment though a portion of the chest (e.g., a thoracotomy) with an affixation mechanism adapted to mechanically couple adjacent the lateral wall. Two adjacent locations include the epicardium and the pericardium. The dimensions may be relaxed to a greater extent if the epicardial receives the transducer, and to a lesser extent, to a portion of the pericardium. As is well known, the pericardium is the membranous sac filled with serous fluid that encloses the heart and the roots of the aorta and other large blood vessels. One example of appropriate fixation apparatus for epicedial application is a helical tipped lead that is screwed into the surface of the epicardium. For pericardial fixation a sealing member (e.g., compressible gasket or opposing members on each side of the pericardial sac) may be used in addition to an active fixation member such as a helical tipped lead.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electric signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describe the internal mechanism of the accelerometer, include spring-retained seismic mass. In most accelerometers, acceleration forces a damped seismic mass that is restrained by a spring, so that it moves relative to the casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot, only the seismic mass primary transducer will be discussed.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Thus, those of skill in the art will recognize that while the present invention has been described herein in the context of specific embodiments, it is recognized that numerous variations of these embodiments may be employed without departing from the scope of the present invention. The descriptions provided herein are thus intended to be exemplary, not limiting, with regard to the following claims.

The invention claimed is:

1. A method for assessing ventricular chamber status following delivery of a refractory period stimulation (RPS) therapy, comprising:
   sensing contraction of a portion of a ventricular chamber of a heart during at least part of the refractory period of the chamber during delivery of a refractory period stimulation (RPS) therapy with a deployed movement transducer and for measuring a signal from the transducer related to the sensed movement;
   coupling said signal to a means for detecting the sensed movement during said refractory period of the chamber, wherein the RPS therapy comprises at least one pulse and is delivered during said refractory period of said chamber;
   filtering the signal obtained during the period of time; and
   one of determining, storing, and programming a logical flag relating to whether or not the ventricular chamber was captured by the RPS therapy.

2. A method for determining the configuration, sequence, waveform, polarity, duration, or timing for delivering left ventricular (LV) electrical pulses and measuring the incidence of mechanical capture and non-capture events due to pacing therapy delivery and refractory period stimulation (RPS) therapy delivery during a given cardiac cycle, comprising:

disposing a transducer that is adapted to directly sense movement of a portion of a LV chamber of a heart and providing a signal related to the movement;

coupling said signal to a means for detecting the movement during at least a part of the refractory period of the LV chamber subsequent to delivery of at least one refractory period stimulation pulse; and one of determining, storing, and programming a logical flag relating to whether or not the LV chamber contracted due to delivery of the at least one refractory period stimulation pulse.

3. A method according to claim 2, wherein said transducer is adapted to be disposed in a portion of one of the coronary sinus vessel and a blood vessel fluidly coupled to said coronary sinus.

4. A method according to claim 3, wherein said transducer comprises an accelerometer.

5. A method according to claim 4, wherein the accelerometer comprises a uniaxial accelerometer having a longitudinal sensing axis substantially aligned toward the left ventricular apex portion of the heart.

6. A method according to claim 3, wherein said transducer comprises a biaxial accelerometer.

7. A method according to claim 3, wherein said transducer comprises a triaxial accelerometer.

8. A method according to claim 2, wherein said transducer is adapted to be disposed adjacent to a portion of the epicardium of the left ventricle of the heart.

9. A method according to claim 8, wherein the portion of the epicardium is a portion of the lateral wall of the left ventricle.

10. A method according to claim 9, wherein the portion of the lateral wall is a basal portion of the lateral wall.

11. A method according to claim 10, wherein the portion of the lateral wall is a mid-basal portion of the lateral wall.

12. A method according to claim 2, wherein said transducer is adapted to be disposed within the pericardium of the heart.

13. A method for determining the configuration, sequence, waveform, polarity, duration, or timing for delivering left ventricular (LV) electrical pulses and measuring the incidence of mechanical capture and non-capture events due to pacing therapy delivery and refractory period stimulation (RPS) therapy delivery during a given cardiac cycle, comprising:

disposing a transducer that is adapted to directly sense movement of a portion of a LV chamber of a heart and providing a signal related to the movement;

coupling said signal to a means for detecting the movement during at least a part of the refractory period of the LV chamber subsequent to delivery of at least one refractory period stimulation pulse; and one of determining, storing, and programming a logical flag relating to whether or not the LV chamber contracted due to delivery of the at least one refractory period stimulation pulse;

wherein said transducer is adapted to be disposed in a portion of one of the coronary sinus vessel and a blood vessel fluidly coupled to said coronary sinus wherein said transducer comprises an accelerometer, and wherein the first pacing electrode or the second pacing electrode further comprises a sense electrode in electrical communication with a sensing circuit.

14. A computer readable medium programmed with instructions for determining the configuration, sequence, waveform, polarity, duration, or timing for delivering left ventricular (LV) electrical pulses and measuring the incidence of mechanical capture events during the refractory period for a given cardiac cycle, comprising:

instructions for sensing movement of a portion of a LV chamber of a heart and providing a signal related to the movement;

instructions for coupling said signal to a means for detecting the movement during at least a part of the refractory period of the LV chamber subsequent to delivery of at least one refractory period stimulation pulse; and instructions for one of determining, storing, and programming a logical flag relating to whether or not the LV chamber contracted due to delivery of the at least one refractory period stimulation pulse.

15. A computer readable medium according to claim 14, wherein said transducer is adapted to be disposed in a portion of the coronary sinus vessel or a blood vessel fluidly coupled to said coronary sinus.

16. A computer readable medium according to claim 15, wherein said transducer comprises an accelerometer.

17. A computer readable medium according to claim 16, wherein the accelerometer comprises a uniaxial accelerometer having a longitudinal sensing axis substantially aligned toward the left ventricular apex portion of the heart.

18. An apparatus for confirming capture of a left ventricular (LV) chamber due to LV pacing stimulus delivery and confirming non-capture due to delivery of refractory period stimulation (RPS) therapy, comprising:

transducer means for measuring movement of a portion of the lateral wall of a LV chamber during a refractory period and providing a movement signal related to such movement;

a movement measurement circuit operatively coupled to the transducer means;

a pulse generator coupled to the measurement circuit;

a left pacing electrode in electrical communication with a portion of the LV chamber and electrically coupled to a RPS therapy delivery circuit of the pulse generator; and an LV chamber movement threshold circuit coupled to the movement signal and adapted to generate a signal relating to one of a capture and non-capture of the LV chamber by the RPS therapy delivered during the refractory period.

19. An apparatus according to claim 18, wherein the pulse generator comprises an implantable pulse generator.

* * * * *